United States Patent [19]
Donelson

[11] Patent Number: 5,409,450
[45] Date of Patent: Apr. 25, 1995

[54] CERVICAL BRACE

[76] Inventor: Ronald Donelson, 3736 Sweet Rd., Jamesville, N.Y. 13078

[21] Appl. No.: 121,536

[22] Filed: Sep. 16, 1993

[51] Int. Cl.$^6$ ............................................. A61F 5/00
[52] U.S. Cl. ...................................... 602/18; 602/19; 602/17; 128/DIG. 23
[58] Field of Search .................................. 602/17–19; 128/DIG. 23; 2/44, 45, 92

[56] References Cited

U.S. PATENT DOCUMENTS

| | | | |
|---|---|---|---|
| 2,692,595 | 10/1954 | Blair, Jr. | 602/17 |
| 2,735,424 | 2/1956 | Benjamin . | |
| 2,736,314 | 2/1956 | Hale . | |
| 2,796,866 | 6/1957 | Cohen | 602/17 X |
| 2,904,040 | 9/1959 | Hale . | |
| 4,141,368 | 2/1969 | Meyer | 602/18 |
| 4,267,830 | 5/1981 | Vick | 602/19 |
| 4,312,334 | 1/1982 | Munoz | 602/19 |
| 4,913,135 | 4/1990 | Mattingly | 602/18 |
| 5,003,968 | 4/1991 | Mars . | |
| 5,046,490 | 9/1991 | Young et al. . | |
| 5,069,449 | 12/1991 | Wardwell | 602/19 X |
| 5,201,702 | 4/1993 | Mars | 602/17 |

FOREIGN PATENT DOCUMENTS 2234905 2/1991 United Kingdom ............... 602/17

Primary Examiner—Linda C. M. Dvorak
Attorney, Agent, or Firm—Charles S. McGuire

[57] ABSTRACT

A cervical brace for painful cervical disorders and injuries includes an elongated, posterior stabilizer molded to the shape of the wearer's posterior occipital, cervical and thoracic surfaces when in the medically desirable position characterized by the shoulders being in a square "military" position and the head retracted with the ear lobes over the superior point of the shoulders. The inferior portion of the stabilizer is fixed against the wearer's upper and mid-thoracic region by a pair of adjustable arm loops and optional trunk strap which also bring and maintain the shoulders to the square "military" position. A chin strap is attached to the superior portion of the stabilizer and is operable to apply a force posteriorly at the chin to draw the head posteriorly toward the superior portion of the stabilizer. A fulcrum is thus created at the cervicothoracic junction with the posteriorly directed force created at the chin counteracted by the anteriorly directed force of the inferior portion of the stabilizer against the mid-thoracic region. The stabilizer levers across the fulcrum point to maintain the head and cervical region in the medically desirable position.

11 Claims, 3 Drawing Sheets

CERVICAL BRACE

BACKGROUND OF THE INVENTION

This invention relates to cervical braces and, more particularly, to a novel and unique cervical brace which achieves and maintains a specific alignment of the cervical spine to relieve mechanical stress on the spine and its supporting soft tissue structures during recovery from certain cervical injuries and painful disorders.

Many types of cervical braces have been developed to aid in proper cervical alignment during the recovery process following injury and/or surgery to the soft tissues, bones, and joints of the neck. The principal goal of any cervical brace is to assist in maintaining "proper" cervical alignment despite the usual bodily movements incurred throughout the day and night activities of the wearer, and to accomplish this in the most efficient and comfortable manner possible.

A growing number of spine clinicians and an increasing list of clinical research studies are recognizing the value of maintaining the lower cervical spine in extension by establishing and maintaining the head in a more retracted (posterior) position. This position is achieved by translating the head posteriorly (termed "retraction" in the art) such that the ear lobes are directly superior to the point of the shoulders, while the shoulders remain in a square "military" position (i.e., not drawn forward).

For most soft tissue injuries to the neck, achieving and maintaining this head position allows for more rapid healing and faster recovery, presumably due to the avoidance of additional cumulative stress on the lower cervical spine occurring with the partial, lower cervical flexion that accompanies a protruding head position. This protruded head position occurs as a result of either patient choice and/or habit, the nature of the injury, or consequentially from the nature of the brace selected by the clinician. Rigid control of horizontal and coronal head rotation, and upper cervical flexion and extension, has not been demonstrated to be critical in this type of soft tissue injury.

Other cervical braces, both current and past, typically include a chin support structure to keep the head from dropping forward and to minimize or eliminate head/neck movements in sagittal, axial, and coronal rotation. This is accomplished through use of a chin support rigidly mounted to, and extending upwardly from, an upper body harness. The back of the head is usually likewise supported by a second, posterior support anchored to and extending upwardly from the posterior portion of the harness. The chest and upper and middle back are utilized as anchor points for the chin and posterior supports to provide upward forces at the chin and posterior head, respectively. Examples of such an apparatus may be seen in U.S. Pat. Nos. 2,904,040 to Hale; 2,735,424 to Benjamin; 5,003,968 to Mars; and 5,046,490 to Young et al. Cervical bracing of this type is most commonly utilized for certain fractures but is awkward and bulky to wear. Also, such braces often require the assistance of a second person, or even a professional, to put on and take off, which is a time-consuming task that may detract from compliance. Furthermore, a relaxed wearer's head often still becomes protruded since the upward force provided by the chin supports does not prevent this protrusion.

"Soft" collars, commonly used in the treatment of cervical soft-tissue injuries, often referred to as "whiplash", do not anchor themselves to the thorax. They consist of a padded, wrap-around support that encases only the neck, providing only a moderate hindrance to sagittal (i.e., back and forward) and coronal bending, and minimal hindrance to horizontal rotation. Soft collars also do not limit protrusion of the head which commonly occurs due to the wearer's choice and/or habit.

Lastly, the PHILADELPHIA ® Collar is a semi-rigid, two-piece anterior/posterior clamshell support which gains support and some stability by resting on the shoulders but does not anchor to the thorax. After they are positioned, the two components fix to one another by the use of VELCRO ® fasteners. The collar incorporates the chin by cupping it with the superior extent of the anterior half of the collar. Posteriorly, the collar extends upward to support the lower occiput for greater control of head movement. Due to its rigidity, chin control, occiput support, and contoured support over the shoulders it is much more effective than the soft collar at hindering rotational movement in all planes. It does not, however, adequately control protrusion.

SUMMARY OF THE INVENTION

It is therefore a principal object of the present invention to provide a cervical brace apparatus which effectively establishes and maintains the head in a retracted position, as viewed from the lateral perspective, thus establishing a greater element of extension within the alignment of the lower cervical spine than patients typically achieve themselves, or by using any other cervical collar apparatus.

It is a further object of the present invention to provide a cervical brace which is relatively simple in design and construction, and which is also quick and easy for the unassisted patient to put on and take off.

It is yet a further object of the present invention to provide a cervical brace which is not bulky and is comfortable to wear.

It is still a further object of the present invention to provide a cervical brace which substantially prevents the patient's head from falling or moving forward when the wearer is relaxed.

Other objects will in part be obvious and in part appear hereinafter.

In accordance with the foregoing objects, the invention comprises a cervical brace having an adjustable shoulder harness, posterior stabilizer, a chin strap, and an optional trunk strap.

The stabilizer is molded from a rigid material (e.g., thermoplastic) into the general shape of the posterior occiput, cervical, and thoracic surfaces created by the desired head position. The stabilizer extends superiorly as a vertical "up-rigger" with its upper-most or superior portion lying posterior to the lower occipital region, and its lower-most or inferior portion lying posteriorly to the upper and mid-thoracic region.

The shoulder harness is composed of two adjustable arm loops which extend from opposite sides of the inferior portion of the stabilizer, anteriorly through the wearer's axillae and then upwardly over the top of each shoulder. The second ends of the arm loops are then adjustably attached to opposite sides of the upper portion of the stabilizer at cervicothoracic level. This adjustable attachment allows for selective tightening of each loop to attain the desired square "military" shoulder position, while securing the inferior portion of the stabilizer against the upper and mid-thoracic spine.

An optional trunk strap is provided at the inferior portion of the stabilizer to assist in maintaining the inferior extent of the stabilizer against the wearer.

An adjustable length chin strap is attached to the superior portion of the posterior stabilizer. The chin strap is positioned to horizontally encircle the patient's head at chin level, engaging the front of the chin with a contoured chin piece. Adjustment of the properly placed chin strap length allows an appropriate amount of posteriorly-directed force to be applied to the head and chin, whereby the head is drawn posteriorly (retracted) toward the superior portion of the fixed posterior stabilizer.

By securing the inferior portion of the stabilizer to the mid-thorax with the arm loops and optional trunk strap, a fulcrum is created at the cervicothoracic junction by the contour and the substantially vertical positioning of the stabilizer on the body. This fulcrum does not become functional until the head is drawn posteriorly by the chin strap. The force required to achieve this retracted head position is counteracted by the full length of the stabilizer levering across the cervicothoracic fulcrum point as the inferior portion of the stabilizer is fixed by the arm loops and optional trunk strap to prevent posterior displacement of the stabilizer away from the thoracic region.

Pulling the head posteriorly effectively draws the lower cervical spine out of flexion and into relative extension, thus creating and maintaining the lower cervical lordosis. As such, the cervical region of the patient is braced in the desirable position by the full combination of elements of the inventive brace, as will be set forth more clearly below.

DETAILED DESCRIPTION

Figure 1:
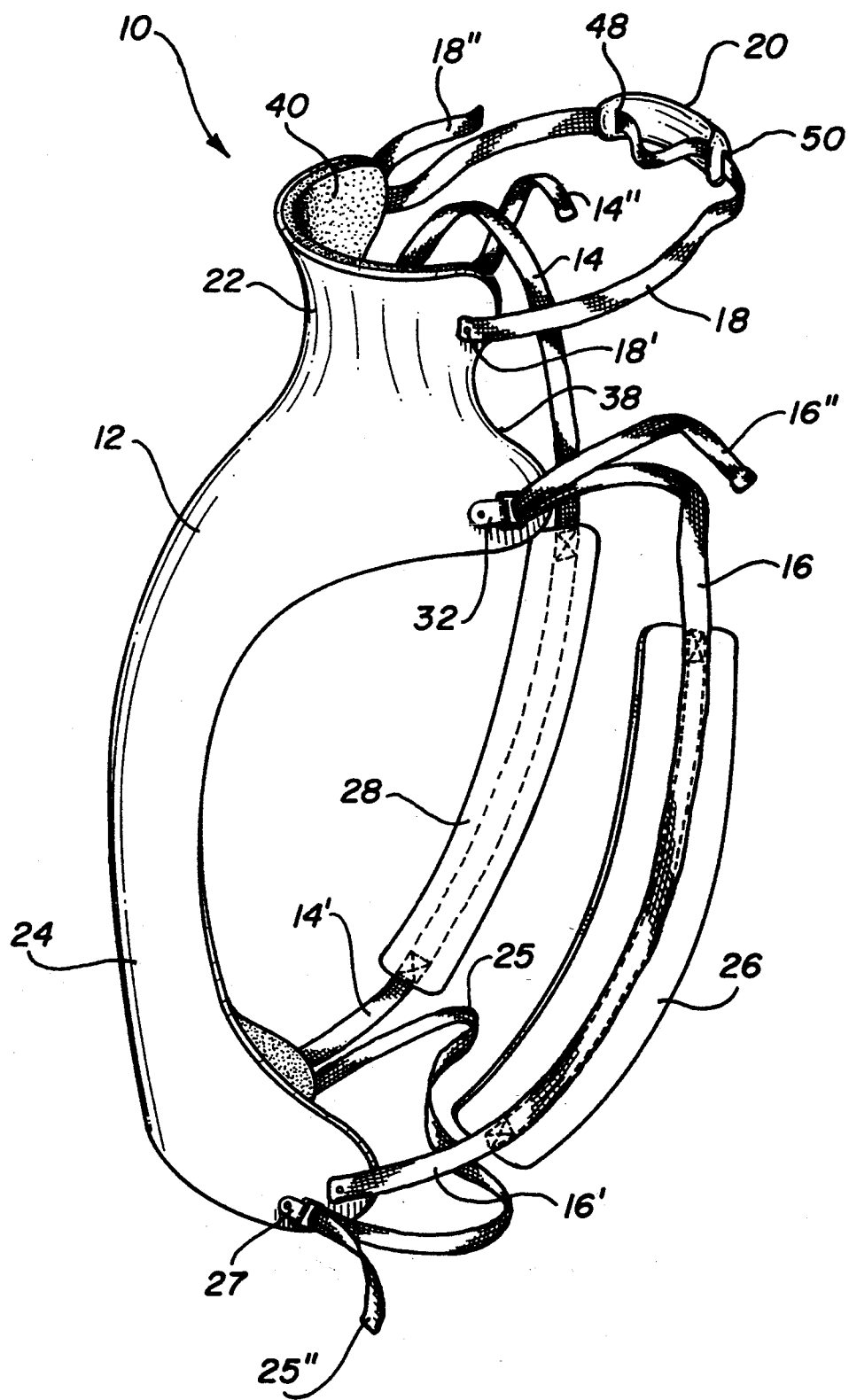
FIG. 1 is a perspective view of the cervical brace.

Referring now to the drawings, there is seen in the various Figures a cervical brace apparatus designated generally by the reference numeral 10.

Brace 10 is comprised of five basic elements which are: 1) a posterior stabilizer 12; 2) first and second, bilateral arm loops 14 and 16, 3) a chin strap 18, 4) a contoured chin piece 20; and 5) an optional trunk strap 25.

Figure 2:
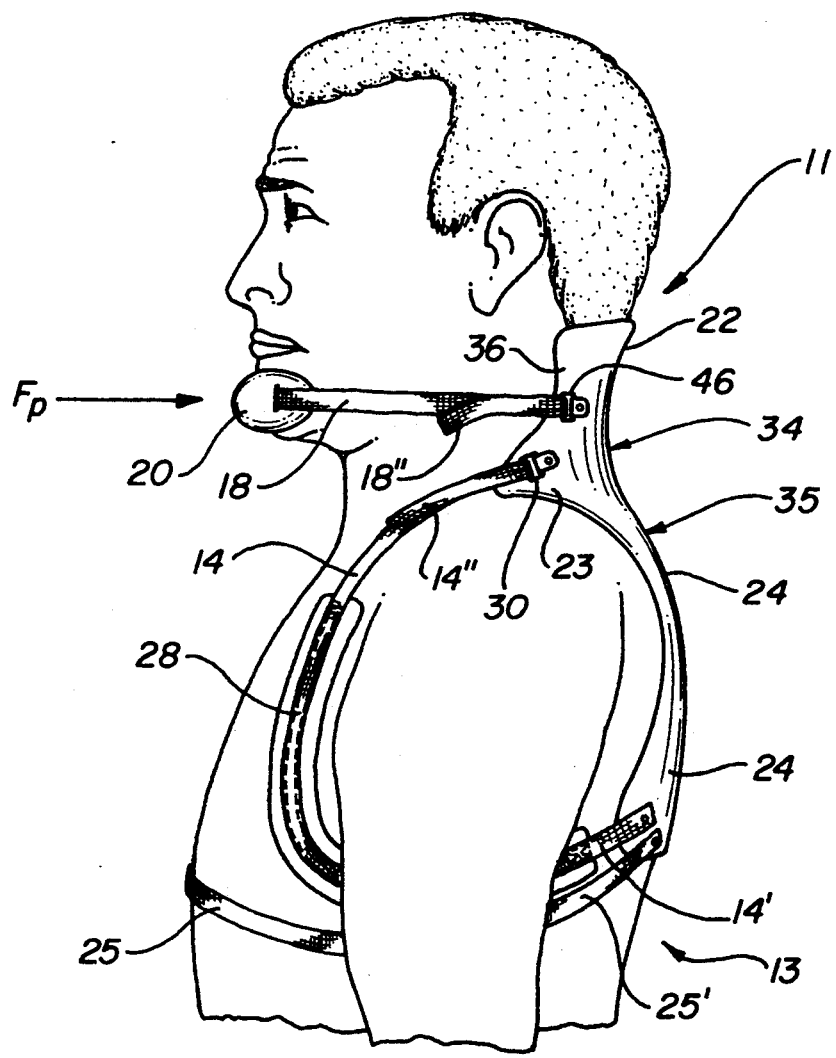
FIG. 2 is a partial side, elevational view of a person wearing the cervical brace in the intended manner.
Figure 3:
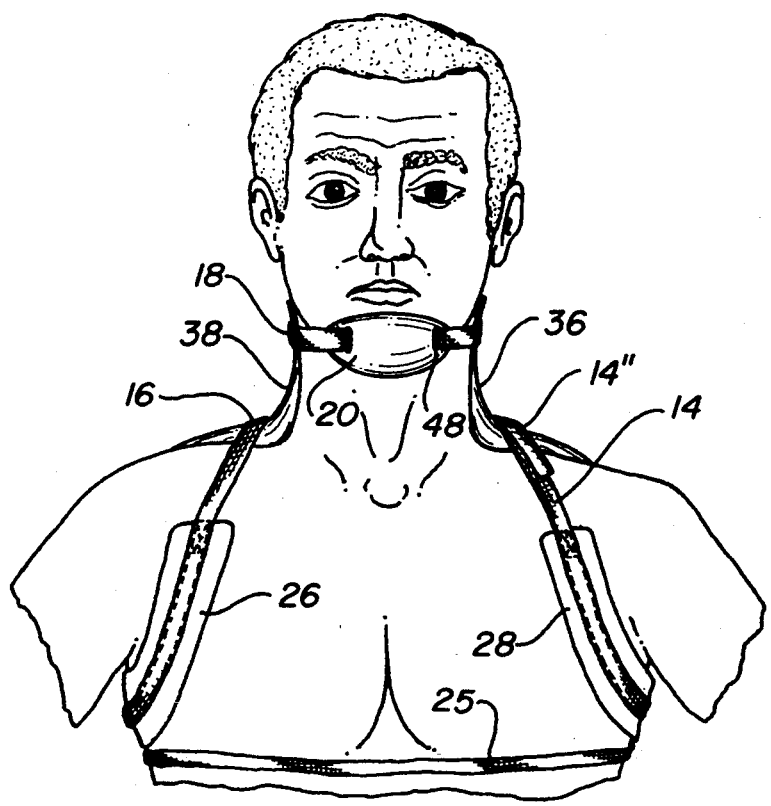
FIG. 3 is a front elevational view thereof.
Figure 4:
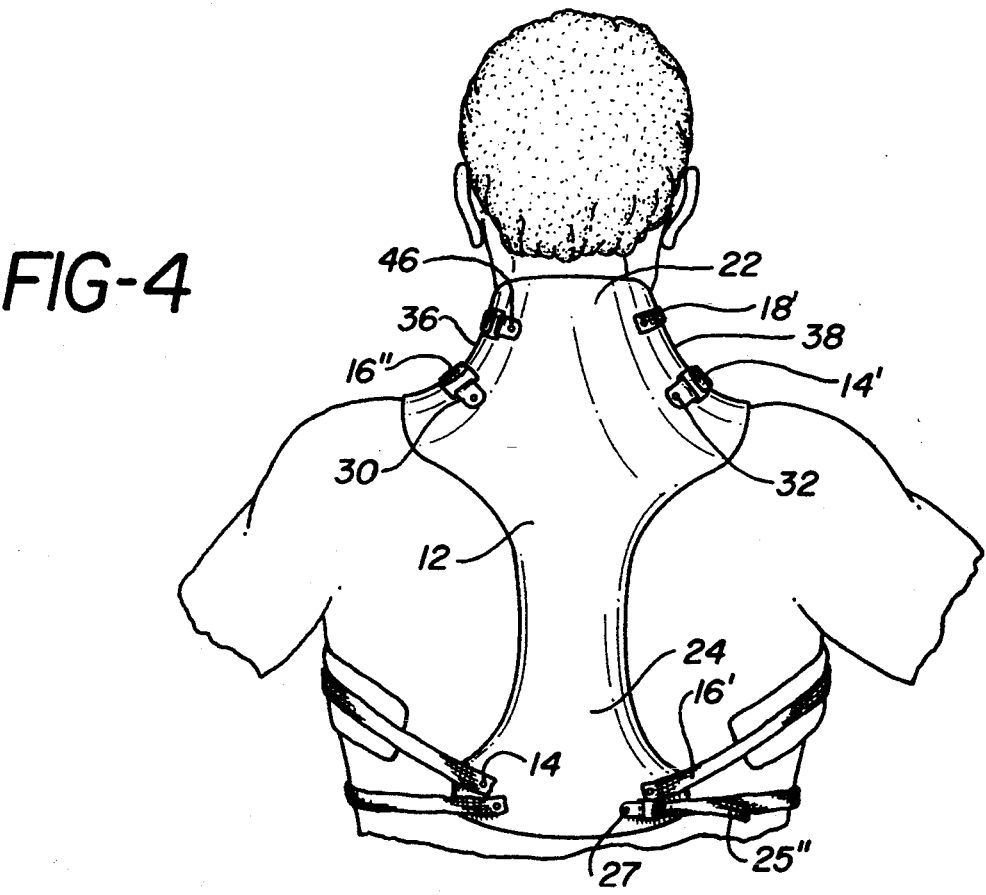
FIG. 4 is a rear elevational view thereof.

Generally speaking, when brace 10 is donned as shown in FIGS. 2, 3 and 4, the patient's shoulders are drawn back to a square "military" position by the arm loops 14 and 16 and a posteriorly-directed force Fp is provided at the chin in accordance with the directional arrow of FIG. 2. The patient's head is thus drawn and maintained posteriorly toward the superior portion 22 of the posterior stabilizer 12 to achieve the desired cervical alignment.

The inferior portion 24 of the posterior stabilizer 12 is anchored to the upper and mid-thoracic region by the arm loops 14 and 16, which pass anteriorly about the shoulders, and the optional trunk strap 25. This anchoring of the inferior portion 24 of stabilizer 12 provides an anteriorly-directed force Fa which counters the posterior retraction force Fp applied to the chin through the fulcrum at the cervicothoracic junction.

The cervicothoracic portion of the posterior stabilizer 12 provides the fulcrum against the cervicothoracic junction 35 allowing the anchored inferior portion 24 of the stabilizer 12 to lever through force $F_a$ across this fulcrum to provide a stable, posterior position for the upper portion of the stabilizer 12 from which the necessary retracting force Fp is applied to the chin. The inferior force $F_a$ counteracts, through the cervicothoracic fulcrum, the anteriorly-directed pull on the superior portion 22 of the stabilizer 12 which occurs with displacement of the head posteriorly through the action of the chin strap 18, enabling the desired head position and extension of the lower cervical spine.

Arm loops 14 and 16 are formed strap-like from flexible material and padded with a soft fabric material (e.g., cotton) 26 and 28, respectively. First ends 14' and 16' of loops 14 and 16 fixedly attach to opposite sides of inferior portion 24 of stabilizer 12, then pass anteriorly through the wearer's axillae, superiorly across the front of the shoulders and then posteriorly over the top of the shoulders to adjustably attach at second ends 14" and 16" to anterior extensions 36 and 38 of stabilizer 12, respectively, for example, by ring fasteners 30 and 32.

The trunk strap 25 is provided if needed to increase the anteriorly-directed force Fa by more firmly anchoring inferior portion 24 of stabilizer 12 against the upper and mid-thoracic region. Trunk strap 25 is fixedly attached at a first end 25' thereof to one side of inferior portion 24 with the second end 25" thereof being adjustably attached to the opposite side of inferior portion 24.

Referring particularly to FIGS. 2 and 4, the posterior stabilizer 12 is seen to be contoured to closely fit the wearer's posterior surface from the lower occiput region 11 to the mid-thoracic region 13 when in the medically desirable head position. Specifically, the superior portion 22 thereof is contoured against the inferior occiput of the head, curved anteriorly at its lower cervical region 34 to contour to the cervical lordosis, with its inferior portion 24 contoured against the upper and mid-thoracic regions, anchored snugly to it by the arm loops 14 and 16 and optional trunk strap 25.

Opposite sides 36 and 38 of the superior portion 22 of stabilizer 12 extend anteriorly with opposite ends of chin strap 18 attaching thereto above second ends 14" and 16" of arm loops 14 and 16, respectively. Particularly, the chin strap 18 is fixedly attached at a first end 18' thereof to the outer surface of anterior extension 38. The second, opposite end 18" of the strap 18 is adjustably attached to the outer surface of anterior extension 36 of the stabilizer 12 whereby chin strap 18 may be selectively tightened to draw the chin and head posteriorly to the retracted position.

Figure 5:
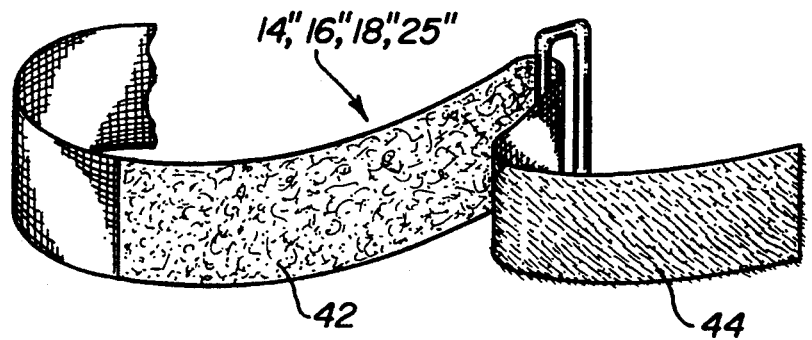
FIG. 5 is a fragmented, perspective view of the adjustable end of the arm loops and chin strap.

An example of adjustable securing means for arm loop ends 14" and 16", chin strap end 18", and trunk strap end 25" may be seen in FIGS. 2, 4 and 5. In FIG. 5, the outer surface of the strap ends are provided with longitudinally adjacent hook and pile VELCRO® patches 42 and 44, respectively, which ends are passed through a respective ring fastener 32, 30, 46 and 27, which themselves are attached to the outer surfaces of anterior extensions 38, 36, and inferior portion 24 of stabilizer 12, respectively. With the strap ends passed through their respective ring fastener, they are doubled back upon themselves to removably engage the hook and pile patches 44 and 42 together, respectively. It is of course understood that other types of strap adjustment means may be desired and that the VELCRO® and ring fasteners herein described are but one preferred way of providing such adjustability to strap ends 14", 16", 18", and 25".

A contoured chin piece 20 includes apertures 48 and 50 wherethrough chin strap 18 is fed such that chin piece 20 is slidable along chin strap 18 to comfortably engage the wearer's chin as the strap 18 is tightened and the head is drawn posteriorly.

The posterior stabilizer 12 is formed from a rigid material such as a thermo-set plastic and is attached in mating engagement to a cooperatively formed liner 40 which is formed from a soft, resilient yet dense padding material. To ensure proper fitting of the stabilizer 12 to the patient, it may be desirable to vary the thickness of the superior and/or inferior portions of liner 40, thus allowing appropriate adjustment of the fulcrum and its position at the cervicothoracic junction 35 to assist in the subsequent positioning of the head. The posterior stabilizer 12 and liner 40 are thus both cooperatively formed into the shape of the patient's anatomically correct posterior cervical surface to provide a brace and support for achieving the desired posterior (retracted) head position.

To don brace 10, the patient begins by passing his/her arms through loops 14 and 16, one at a time. Each loop is then tightened to achieve the square "military" shoulder position. Adjustment of arm loops 14 and 16 upon and by the patient orients the posterior stabilizer 12 vertically so its superior portion 22 is in the vicinity of the base of the lower occiput. If needed, trunk strap 25 is wrapped around the wearer's trunk and tightened.

Chin strap 18 and chin piece 20 may then be positioned and secured about the chin of the patient with the chin piece 20 engaging the front of the chin below the lower lip. Its length is adjusted to apply force Fp to achieve the desired head position.

To briefly summarize, arm loops 14 and 16 draw the shoulders backward as well as anchor the inferior portion 24 of the stabilizer 12 to the posterior, upper and mid-thoracic region. With the stabilizer 12 positioned in the desired, fixed position, a fulcrum is created at the cervicothoracic junction 35. Chin strap 18 creates a posterior force Fp at the patient's chin which is counteracted by the anterior pull and stabilization of the inferior portion 24 of stabilizer 12 by arm loops 14 and 16 and optional trunk strap 25. The lower cervical region is thus correctly aligned.

The invention has been described with particular references to a preferred embodiment thereof. It will be appreciated to those skilled in the art that various modifications may be made to the invention without departing from the full spirit and scope thereof as defined by the claims which follow.

What is claimed is:

1. A cervical brace to be worn in a manner maintaining the wearer in a position with shoulders square and head retracted, said brace comprising:
   a) a unitary, substantially rigid body member generally elongated along a centerline between upper and lower ends, said body member including:
      i) a superior portion having right and left sides and extending downwardly from a top edge at said upper end;
      ii) an inferior portion having right and left sides and extending upwardly from a bottom edge at said lower end to merge in smooth-surfaced relation with said superior portion; and
      iii) said top edge and adjacent part of said superior portion curving smoothly about the upper end of said centerline to approximate the curvature of the wearer's lower occiput region;
   b) a first, flexible strap having opposite end portions respectively connected to said superior portion right and left sides at positions closely below said top edge;
   c) a second flexible strap having a first portion connected to said superior portion right side at a position below the right side connection of said first strap, and a second portion connected to said inferior portion right side at a position closely above said bottom edge; and
   d) a third flexible strap having a third portion connected to said superior portion left side at a position below the left side connection of said first strap, a fourth portion connected to said inferior portion left side at a position closely above said bottom edge, whereby said first strap is adapted to engage the wearer's chin and hold the head in a retracted position, and said second and third straps are adapted to extend from the wearer's mid-thoracic region, under the arms, to positions above the shoulders, thereby urging the shoulders toward a squared position.

2. The cervical brace of claim 1 wherein said superior portion extends downwardly and outwardly from said upper edge on both said right and left sides of said superior portion to approximate the curvature of the transition of the wearer's neck and shoulders on each side.

3. The cervical brace of claim 2 wherein said inferior portion includes outwardly extending areas on both said inferior portion right and left sides at positions upwardly adjoining said bottom edge and said second and third straps are connected at their respective second and fourth portions to said outwardly extending areas.

4. The cervical brace of claim 1 and further including a fourth strap having opposite portions respectively connected to said inferior portion right and left sides, said fourth strap being adapted to extend about the wearer's torso.

5. The cervical brace of claim 4 and further including means for selectively adjusting the effective lengths of each of said first, second, third and fourth straps.

6. The cervical brace of claim 1 wherein said body member is substantially symmetrical on opposite sides of said centerline.

7. The cervical brace of claim 6 wherein said superior portion extends downwardly and outwardly from said top edge on both said superior portion right and left sides, and thence inwardly to merge with said inferior portion.

8. The cervical brace of claim 6 wherein said top edge lies in a plane transverse to said centerline.

9. The cervical brace of claim 8 wherein said bottom edge lies in a plane transverse to said centerline.

10. The cervical brace of claim 1 wherein said body member includes inner and outer surfaces respectively adapted to be directed toward and away from body surfaces of a wearer's body.

11. The cervical brace of 10 and further including resilient padding material affixed in covering relation to at least portions of said inner surface.

* * * * *